United States Patent
Mossig

(10) Patent No.: US 12,070,742 B2
(45) Date of Patent: Aug. 27, 2024

(54) TRANSPORTABLE CLEAN ROOM, METHOD FOR PRODUCING A TRANSPORTABLE CLEAN ROOM, AND METHOD FOR FILLING A MEDICINE CONTAINER IN A TRANSPORTABLE CLEAN ROOM

(71) Applicant: VETTER PHARMA-FERTIGUNG GMBH & CO. KG, Ravensburg (DE)

(72) Inventor: Stefan Mossig, Ravensburg (DE)

(73) Assignee: VETTER PHARMA-FERTIGUNG GMBH & CO. KG, Ravensburg (DE)

(*) Notice: Subject to any disclaimer, the term of this patent is extended or adjusted under 35 U.S.C. 154(b) by 699 days.

(21) Appl. No.: 16/646,602

(22) PCT Filed: Sep. 14, 2018

(86) PCT No.: PCT/EP2018/074872
§ 371 (c)(1),
(2) Date: Mar. 12, 2020

(87) PCT Pub. No.: WO2019/053186
PCT Pub. Date: Mar. 21, 2019

(65) Prior Publication Data
US 2020/0261901 A1    Aug. 20, 2020

(30) Foreign Application Priority Data
Sep. 14, 2017 (DE) .................. 10 2017 216 366.6

(51) Int. Cl.
*B01L 1/04* (2006.01)
*A61L 2/07* (2006.01)
(Continued)

(52) U.S. Cl.
CPC ............... *B01L 1/04* (2013.01); *A61L 2/07* (2013.01); *A61L 2/087* (2013.01); *B01L 9/06* (2013.01);
(Continued)

(58) Field of Classification Search
None
See application file for complete search history.

(56) References Cited

U.S. PATENT DOCUMENTS 2,786,740 A * 3/1957 Taylor .................. B25J 21/02
D24/234
4,804,392 A   2/1989 Spengler
(Continued)

FOREIGN PATENT DOCUMENTS

EP    2871031 A2    5/2015
JP    S62193781 A   8/1987
(Continued)

OTHER PUBLICATIONS

Russian Search Report issued in Russian counterpart application No. 2020113347/04, issued Jul. 19, 2021.
(Continued)

*Primary Examiner* — Holly Kipouros
(74) *Attorney, Agent, or Firm* — Harness, Dickey & Pierce, P.L.C.; Stephen T. Olson

(57) ABSTRACT

The invention relates to a portable clean room for filling at least one medicine container, located in the clean room with at least one active substance, wherein: the clean room is enclosed in an airtight manner by an at least partially flexible shell, the shell has at least one active substance connection region which can be opened, and a manipulation device and at least one medicine container are located in the clean room. According to the invention, the shell has at least one actuation connection region, wherein the manipulation device has at least one filling device which can be coupled to the active substance connection region for introducing at least one active substance into the at least one medicine container arranged in the clean room, and the manipulation device can be actuated by means of an actuation device via the actuation connection region of the shell, and is designed
(Continued)

to displace the filling device—relative to the at least one medicine container—and/or to actuate the filling device.

19 Claims, 1 Drawing Sheet

(51) Int. Cl.
    *A61L 2/08*         (2006.01)
    *B01L 9/06*         (2006.01)
    *B08B 15/02*       (2006.01)
    *B25J 19/00*       (2006.01)
    *B25J 21/00*       (2006.01)
    *F24F 3/167*       (2021.01)

(52) U.S. Cl.
    CPC ......... *B08B 15/026* (2013.01); *B25J 19/0075* (2013.01); *B25J 21/005* (2013.01); *F24F 3/167* (2021.01); *A61L 2202/181* (2013.01); *B01L 2300/123* (2013.01)

(56) References Cited

U.S. PATENT DOCUMENTS

| | | |
|---|---|---|
| 5,685,771 A | 11/1997 | Kleppen |
| 5,881,535 A | 3/1999 | Gliniecki et al. |
| 2002/0105251 A1* | 8/2002 | Kensey ................ B08B 15/026 312/1 |
| 2004/0158121 A1 | 8/2004 | Ford et al. |
| 2006/0119232 A1 | 6/2006 | Tattershall |
| 2008/0216662 A1 | 9/2008 | Koh et al. |
| 2011/0208350 A1 | 8/2011 | Eliuk et al. |
| 2012/0031042 A1 | 2/2012 | Zambaux |
| 2014/0311617 A1 | 10/2014 | Py |
| 2015/0107190 A1* | 4/2015 | Zambaux ................ B25J 21/02 53/287 |
| 2016/0068793 A1* | 3/2016 | Maggiore ............. B29C 64/188 901/22 |
| 2016/0297082 A1* | 10/2016 | Hanley ................ A61G 10/005 |
| 2017/0259438 A1* | 9/2017 | Bihannic ................. F41G 3/145 |
| 2018/0037343 A1* | 2/2018 | Procyshyn ............. B65B 3/003 |

FOREIGN PATENT DOCUMENTS

| | | |
|---|---|---|
| JP | H02107384 A | 4/1990 |
| JP | 3097933 B2 | 10/2000 |
| JP | 2009535015 A | 10/2009 |
| JP | 2012-519599 A | 8/2012 |
| JP | 2013-244340 A | 12/2013 |
| JP | 2015077680 A | 4/2015 |
| JP | 2015104358 A | 6/2015 |
| JP | 2017006990 A | 1/2017 |
| RU | 2626198 C2 | 7/2017 |
| WO | WO-2010100234 A1 | 9/2010 |

OTHER PUBLICATIONS

English Translation of International Preliminary Report on Patentability and Written Opinion issued in PCT/EP2018/074872, mailed Mar. 17, 2020.
International Search Report (in English and German) and Written Opinion (in German) issued in PCT/EP2018/074872, mailed Nov. 27, 2018; ISA/EP.
Japanese Office Action regarding Patent Application No. 2023045907, dated Mar. 5, 2024.
Japanese Office Action regarding Application No. 2020-514938, dated Jul. 18, 2023.

* cited by examiner

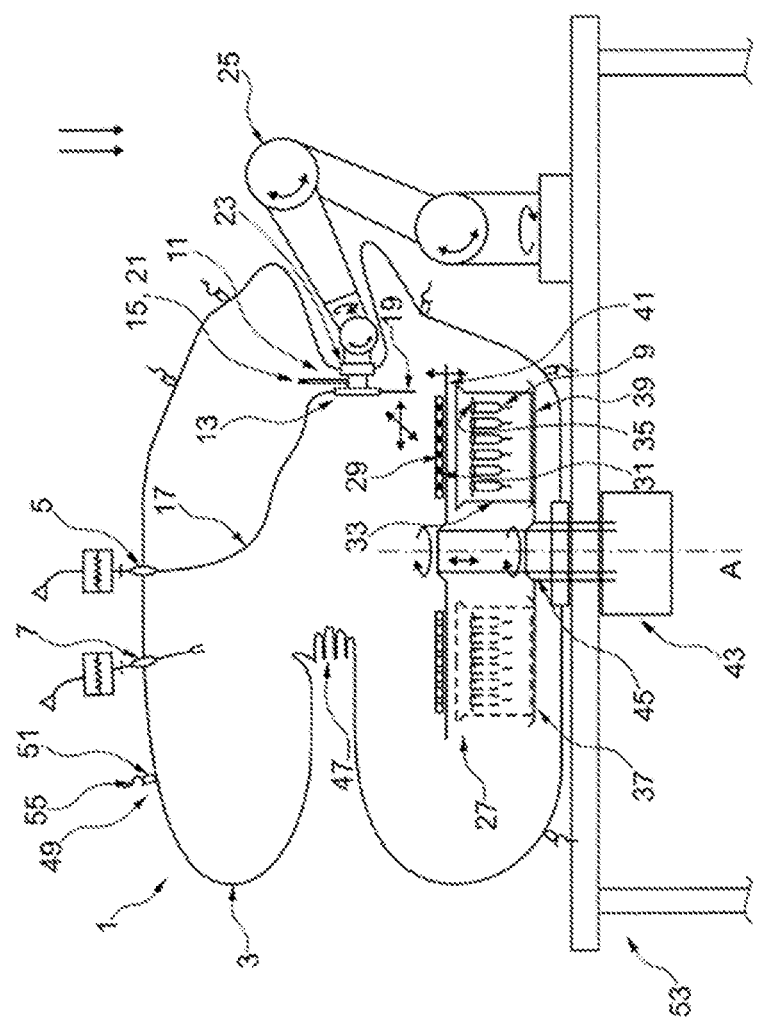

TRANSPORTABLE CLEAN ROOM, METHOD FOR PRODUCING A TRANSPORTABLE CLEAN ROOM, AND METHOD FOR FILLING A MEDICINE CONTAINER IN A TRANSPORTABLE CLEAN ROOM

CROSS-REFERENCE TO RELATED APPLICATIONS

This application is a 371 U.S. National Phase of International Application No. PCT/EP2018/074872, filed Sep. 14, 2018, which claims the benefit of German Patent Application No. 10 2017 216 366.6, filed Sep. 14, 2017. The entire disclosures of the above applications are incorporated herein by reference.

The invention relates to a transportable clean room for filling at least one medicine container located in the clean room with at least one active substance, a method for producing such a transportable clean room and a method for filling a medicine container in such a transportable clean room.

Transportable clean rooms of the type mentioned here are known. Typically, a transparent shell of the transportable clean room is stretched out by means of a flexible or rigid outer support structure. Medicine containers, active substances, filling devices and/or closing devices can be introduced into the clean room via a closable opening of the shell and/or a lock. A human manipulator can fill and/or close the medicine containers by means of intervention gloves formed in the shell and the filling and/or closing devices introduced into the clean room. However, clean rooms of this type can only be operated manually and are therefore complex. In addition, medicine containers to be filled must be introduced into such clean rooms after the clean room has been opened, so that the risk of contamination of the clean room is high. The active substance to be filled must also be introduced via the opening or the lock, which is typically large enough for the human manipulator to reach through it in order to arrange the medicine container or the active substance in the clean room or to remove it from the clean room. The risk of contamination is therefore particularly high, especially if the clean room is used in a non-sterile environment.

The object of the invention is to provide a transportable clean room, a method for producing such a portable clean room and a method for filling a medicine container in such a transportable clean room, the disadvantages mentioned being avoided.

The object is achieved by providing the objects in the independent claims. Advantageous embodiments are described in the dependent claims.

The object is achieved in particular by creating a transportable clean room for filling at least one medicine container arranged in the clean room with at least one active substance, the clean room being enclosed in an airtight manner by an at least partially flexible shell. It is provided that the shell has at least one openable active substance connection region and at least one actuation connection region, in particular a robot connection region, wherein a manipulation device and at least one medicine container are arranged in the clean room. The openable active substance connection region is preferably designed in such a way that at least one active substance can be introduced into the clean room from outside the clean room via the active substance connection region which is in particular sealed in a sterile manner from an external environment. In addition, the manipulation device has at least one filling device which can be coupled to the active substance connection region, preferably coupled to it, for introducing the at least one active substance into the at least one medicine container arranged in the clean room, the manipulation device using an external control device, in particular a robot, via the actuation connection region, in particular the robot connection region, of the shell being actuatable, and being set up to displace the filling device—relative to the at least one medication container—and/or to actuate the filling device. Such a transportable clean room increases the automation of the filling of medicine containers with at least one active ingredient and is therefore particularly efficient. Medicine containers can thus be filled quickly and inexpensively, the risk of contamination being reduced due to the complete sealing to the outside which also exists during the filling of the medicine container.

The manipulation device itself, particularly preferably together with the filling device, can preferably be displaced by means of the preferably automated actuating device, in particular the robot. Alternatively or additionally, the manipulation device is at least partially automated, particularly preferably fully automated, so that the displacement and/or the actuation of the filling device can be carried out automatically. For the automated actuation of the manipulation device, in particular a robot arm of a robot is provided which, after coupling with the manipulation device, is set up to displace the manipulation device. For automated actuation of the filling device, the actuation connection region preferably has at least one signal transmission element, in particular signal cable and/or signal cable connection, for the transmission of in particular electrical, hydraulic and/or pneumatic signals. The at least one signal transmission element is set up to forward a signal supplied by the actuating device to the in particular automated filling device. The automation of the filling is therefore very high—especially when the manipulation device is actuated by means of the robot—and the filling can be carried out efficiently.

The clean room is preferably transportable in such a way that it can be carried by a person. The clean room therefore preferably has a weight and volume that can be carried by a person. The weight is particularly preferably less than 100, preferably less than 10 kg and the volume of the clean room less than 4 m³, preferably less than 2 m³, preferably less than 1 m³, preferably less than 0.5 m³, preferably less than 0.15 m³, preferably less than 0.03 m³.

The shell of the clean room preferably has no passage, in particular no door, for people to enter and/or leave the clean room. The clean room is therefore not accessible by foot. An action on the interior of the clean room, in particular mechanical manipulation of the medicine container and/or actuation of a device arranged in the clean room, is preferably only possible via connection regions, in particular the active ingredient and/or actuation connection region, and/or the at least partially flexible shell, in particular the flexible part of the shell, very particularly a part of the shell designed for manual intervention with the interior of the clean room, and/or a passage in the shell.

A medicine container is understood here to mean in particular an ampoule, a vial, a syringe or a cartridge. A plurality of such medicine containers is preferably arranged in the clean room. A small number of medicine containers, in particular for use in personalized medicine, are particularly preferably arranged in the clean room. It is therefore possible to fill the small number of medicine containers individually for a patient. Alternatively, it is provided that a large number of medicine containers, in particular for use in the mass market, are arranged in the clean room.

The medicine container is preferably at least partially prefilled with a substance, in particular an additional medical auxiliary and/or active substance. The substance preferably has—at least in the cleanliness class present in the clean room—a long shelf life, so that it can be stored in the medicine container in the clean room for a large number of days, weeks, months and/or years without the durability being endangered, in particular without exceeding a best-before date and/or an expiration date for the substance. The substance is preferably provided for mixing with the active ingredient, as a result of which a specific medicinal effect is achieved. The substance is preferably arranged in a first chamber of the medicine container, the first chamber being closable by means of a closure element at least during storage and/or transport of the clean room.

The closure element is preferably mounted so that it can be removed, so that before the medicine container is filled, the first chamber is opened by removing the closure element, in particular by means of the manipulation device, and the first chamber can be filled by means of the filling device, the substance mixing with the active substance. Thus, a pre-filling with the substance can take place separately in time and/or space from the filling with the active substance, the at least one pre-filled medication container being able to be stored in the clean room for a long time, in particular several days, weeks, months or years, and being transported with little effort. The pre-filling with the substance during the production of the clean room is carried out in particular in a clean environment, very particularly in a stationary clean room. The filling with the active ingredient is carried out at a later time in the finished clean room, preferably in an impure environment. Since the provision of the clean environment is expensive and involves a great deal of effort, the costs for filling the medicine container, in particular partially pre-filled, with the active substance in an impure environment are reduced.

The medicine container is preferably designed as a multi-chamber system, in particular a double-chamber system, the substance being arranged in the first chamber and a second chamber of the medicine container being set up for filling with the active substance by means of the filling device. In this case, the closure element is preferably designed as a displaceable separating element, which separates the first chamber from the second chamber in terms of flow technology, wherein a fluidic connection between the chambers is possible by moving the separating element via a bypass. In addition, a further closure element is preferably provided for closing the second chamber, which is also removably mountable such that it can preferably be removed by means of the manipulation device before the second chamber is filled. Such multi-chamber systems are already known, so that their functioning will not be discussed further at this point.

An actuating device is understood here to mean in particular a partially automated or fully automated actuating device, very particularly a robot. The actuating device is set up to actuate the manipulation device mechanically and/or electrically. The actuating device is preferably set up to carry out a repetitive, in particular regular movement, in particular of an actuating arm, very particularly of a working or robot arm, in order to actuate, in particular to displace, the manipulation device. Alternatively or additionally, the actuating device is set up to send at least one electrical signal, preferably a regular sequence of electrical signals, to the manipulation device in order to actuate the manipulation device in such a way that it carries out a mechanical movement and/or transmits an electrical signal.

An actuation connection region is understood here to mean in particular a connection region for the, in particular, automated actuation device. An actuation connection region is particularly understood to mean a robot connection area.

The shell is preferably so flexible that it is collapsible. The clean room is further preferably enclosed in an airtight manner by the shell such that the shell can be inflated and/or evacuated. It is therefore preferably possible for a vacuum to be applied to the clean room in such a way that the shell collapses. This reduces the need for storage space for such clean rooms.

The clean room is particularly preferably provided for transport and/or storage, in particular for long, very particularly several years of storage, in a non-sterile, in particular impure, environment. During such storage, the cleanliness of the clean room is not reduced, since the shell encloses the clean room in an airtight manner. Alternatively or in addition, the clean room is intended for use, in particular for filling the medicine container, in a non-sterile environment. It is thus possible to decouple the production of the clean room, the storage of the clean room, the transport of the clean room and the filling of the medication container in the clean room from one another in terms of time and/or location, without the costs being high, since a clean environment is not required for all steps. In particular, the storage and transportation of such a clean room can take place in an impure environment without endangering the cleanliness of the interior of the clean room. Such a clean room can thus be produced in a clean environment in a first step, then stored and/or transported in an impure environment for a long time, in a second step, until finally the medication container in the clean room can be filled in a third step. During the third step, the clean room is preferably arranged in a clean environment. During the second step, the clean room is preferably arranged in an impure environment. Thus, the costs of storage and/or transportation, and thus also the total costs of the first step, the second step and the third step—both with a spatial separation and with a temporal separation of the first step from the third step—are low. In addition, a process chain that encompasses all three steps can be flexibly adapted. In particular, the production of the clean room, in particular in large numbers, can be carried out at a central manufacturing location and—after transport to a filler—the medicine containers can be filled, in particular a small number of clean rooms, particularly a single clean room, at a decentralized filling location at the filler.

A clean environment is understood here to mean in particular an environment on which purity requirements are imposed. Such purity requirements include, in particular, limit values for particle size distributions and/or bacterial counts, the limit values typically being specified by a purity classification, such as the EU GMP classification or DIN EN ISO 14644-1. An impure environment is understood here to mean in particular an environment on which no purity requirements are imposed. Although it is possible that an impure environment also complies with the limit values of a purity classification, compliance with these limit values in the impure environment is not required. In particular, no precautions have been taken to comply with these limit values in an impure environment.

The shell of the clean room preferably has no opening, in particular no closable opening, through which the at least one medicine container or another medicine container and/or tools can be introduced into the clean room. The shell particularly preferably has no closable opening through which a human manipulator can reach through manually.

Alternatively or additionally, the clean room has no lock. This increases the safety of the clean room and reduces the risk of contamination.

The clean room preferably has at least one active substance line, in particular active substance hose, for the fluidic flow of the active substance from the active substance connection region to the filling device, the active substance line preferably being flexible and/or foldable. The active substance line is preferably designed as an internal active substance line, which fluidically connects the active substance connection area with the filling device and is arranged in the interior of the clean room. In addition, the active substance connection region is particularly preferably set up in order to be connected in terms of flow technology by means of an externally designed active substance line to an external active substance supply device, which preferably has a quantity of active substance required for filling a large number of medicine containers. In the connected state, the active substance supply device is preferably set up to provide the active substance in particular by means of an active substance pump and/or to transmit it to the filling device. Particularly in the case of an automated design of the manipulation device, a very efficient filling of the medicine container is possible.

The active substance connection region is preferably designed as a coupling element which, in the inward direction, has an inner connection area for, in particular, tensile and/or pressure-resistant coupling to the internal active substance line and/or, in the outward direction, has an outer connection area for in particular tensile- and/or pressure-resistant coupling to the external active substance line, the internal and the external active ingredient line being preferably formed separately from one another. The coupling is—at least in the direction inwards or outwards, in particular in the direction of the fluidic connection—preferably designed as a form-fitting coupling, in particular as a screw and/or snap coupling. Alternatively, the active substance connection region is cohesively connected to the active substance line, in particular formed integrally with it. This prevents the active substance line from becoming detached when the shell is displaced in the region of the active substance connection region and/or when a tensile and/or compressive force is applied, in particular in the direction inwards or outwards.

As an alternative or in addition, the clean room, in particular the active substance connection region and/or the at least one active substance line, very particularly the internal active substance line and/or the external active substance line, has at least one active substance valve which can be actuated particularly preferably automatically, in particular by means of the manipulation device and/or the active substance supply device and when actuated releases and/or blocks the fluidic connection, in particular between the filling device and the active substance connection region and/or between the active substance connection region and the external active substance supply and/or between the filling device and active substance supply. This ensures a very safe and, in particular, automated supply and delivery of active ingredients.

The clean room is sealed completely and in a sterile manner against an external environment of the clean room even during the filling of the medicine container. The active substance connection area is designed such that it is closed both airtight and thus sealed in a sterile manner in its closed state, as well as in its open state, which is connected in particular to an external active substance connection and to the filling device, in such a way that it supplies the at least one active substance allowed in the clean room, but at the same time still seals it airtight and in a sterile manner to the outside. The active substance connection region thus represents in particular a sterile conduit for introducing the active substance into the interior of the clean room. The at least one actuation connection region, in particular a robot connection region, is also designed in such a way that the manipulation device can be coupled via the actuation connection region to at least one external actuation device, in particular a robot, which is arranged outside the clean room, in such a way that the interior of the clean room is sterile and airtight against the exterior, that is, remains sealed against an external environment of the clean room. The actuation connection region represents, in particular, an airtight, sterile mechanical conduit to the outside of the clean room, which is set up for coupling the external actuation device.

A displacement of the filling device—relative to the at least one medicine container—is understood here to mean a displacement in the clean room, which causes the filling device to be moved to a position suitable for filling the medicine container. The filling device, which preferably has a filling needle, can preferably be moved directly over the medicine container. The filling needle particularly preferably penetrates into an interior of the medicine container in order to fill it.

The clean room is preferably set up so that it can be operated in a fully automated manner, in particular for filling the at least one medicine container, at least after the active substance connection region is connected to the external active substance supply and/or the actuation connection region is coupled to the actuating device.

According to a development of the invention, it is provided that the manipulation device has at least one closing device, in particular a stopper device, very particularly a stopper pin, for closing the at least one medicine container with at least one closure arranged in the clean room, in particular for putting on the at least one closure arranged in the clean room on the at least one medicine container, and is set up to displace the closure device—relative to the at least one medicine container—and/or to actuate the closure device. Here, a closure is understood to mean a stopper that can be inserted in particular into the medicine container, a septum or a closure that can be applied from the outside, in particular a cap or a lid. The risk of contamination of the clean room, which exists in particular when a closure is introduced into a classic clean room, is thus reduced, since the closure is already present in the clean room, particularly from the start. The manipulation device therefore has the filling device and the closing device, so that the medicine container in the clean room can be filled and closed.

Alternatively, it is provided that a second manipulation device has the closing device and is set up to displace the closing device and/or to actuate the closing device. The second manipulation device can also be actuated by means of an actuation device, in particular a robot, of the at least one actuation device.

According to a development of the invention, it is provided that a supply device is arranged in the clean room, which provides the at least one medicine container for filling by means of the filling device and/or for closing with the at least one closure, and/or the at least one closure for closing the medicine container provides the closing device. The provision device preferably has a first receiving device, in particular a tub, for receiving the medicine containers and/or a second receiving device for the closure and/or a holding device, in particular a plate system, very particularly a turntable system. The first receiving device receiving the at least one medicine container can preferably be closed by a semipermeable membrane in such a way that sterilization of the medicine container through the semipermeable membrane is possible, but contamination of the medicine container with particles and/or germs through the semipermeable membrane is avoided. The first and/or the second receiving device are preferably held by the holding device, the first receiving device preferably being held by a first support element, in particular for carrying the tub, and/or the second receiving device preferably by a second support element, the first support element and/or the second support element being preferably designed as a plate. Preferably, the first support element and/or the first receiving device and/or the second mounting element and/or the second receiving device can be displaced translationally and/or rotationally, in particular rotatably and/or pivotably, at least relative to an axis of rotation of the provision device. The first supporting element and/or the first receiving device thus serve to provide the at least one medicine container, and the second supporting element and/or the second receiving device serve to provide the at least one closure. The second receiving device is particularly preferably designed as a closure matrix, in particular a stopper matrix, for providing and receiving the at least one closure, in particular a stopper, in which case no second support element is preferably provided. This increases the automation and the efficiency of the filling and reduces the costs.

According to a development of the invention, it is provided that the at least partially flexible shell encloses a first volume in an airtight manner in a first functional state of the clean room, wherein it encloses a second volume in an airtight manner in a second functional state of the clean room, the second volume being larger than the first volume, and is so large that the at least one medicine container can be filled by means of the filling device. In the first functional state of the clean room, the envelope is preferably compact, collapses and/or folds. In the first functional state, the clean room is preferably subjected to a low pressure, in particular a negative pressure, relative to an environment surrounding the clean room. The first volume is preferably less than 1 m$^3$, preferably less than 0.15 m$^3$, preferably less than 0.03 m$^3$. In the second functional state of the clean room, the clean room is preferably subjected to a higher pressure than in the first functional state. In particular, it is subjected to a slight overpressure relative to the external environment. The second volume is preferably less than 4 m$^3$, preferably less than 2 m$^3$, preferably less than 1 m$^3$, preferably less than 0.5 m$^3$. In addition, in the second functional state of the clean room, the shell is at least partially, preferably at least in the area of the actuation connection area, movable in such a way that the filling device and/or the closing device and/or the manipulation device can be moved. This applies in particular if the filling device and/or the closing device are fixedly connected to the manipulation device, the manipulation device in turn being firmly attached to the shell.

According to a development of the invention, it is provided that the shell has at least one air connection region, preferably an openable and/or closable sterile air connection region. The air connection region preferably also has an air filter. This air connection region is particularly preferably designed to supply air to the clean room and/or to remove air from the clean room and/or to move the clean room from the first functional state to the second functional state and/or from the second functional state to the first functional state. This improves the safety of the clean room, with dangerous substances in particular not being able to escape from the clean room, particularly in the event of a leak.

The clean room preferably has an air line, in particular an air hose, for the fluidic control of air, in particular sterile air, from the air connection region into the interior of the clean room, the air line preferably being flexible and/or foldable. The air line is designed as an inner air line and/or as an outer air line, the air connection region being able to be coupled to a particularly automated air supply device, in particular a pump, by means of the outer air line. A particularly automated air supply system is thus created in order to supply air into the clean room and/or remove it from the clean room. Alternatively or additionally, at least one air valve is arranged in the air connection region and/or in the air line, which can be actuated by means of the air supply device and/or the manipulation device and, when actuated, blocks and/or releases the connection between the interior of the clean room and the air connection region and/or between the air connection region and air supply device. The air line particularly preferably has a further air filter. The safety of the clean room and the cleanliness of the clean room are therefore high.

Alternatively or additionally, the at least one air connection region is set up to ensure a laminar air flow in the clean room. For this purpose, a first plurality of, in particular uniformly distributed, air connection regions, in particular on the upper side, is preferably arranged in the shell, in order to preferably supply air coming from above into the clean room. Particularly preferably, a second, corresponding plurality of, in particular uniformly distributed, air connection regions is arranged on the underside, which preferably removes the air homogeneously, in particular downwards, from the clean room. This creates a first plurality of air connection regions and a second plurality of air connection regions, which are preferably arranged opposite one another in the shell of the clean room and—at least in the second functional state—are designed to provide a laminar air flow, in particular from top to bottom.

The air connection region is preferably also set up to apply an overpressure to the clean room. The purity and/or sterility in the clean room is thus increased and the risk of contamination of the medicine container and in particular of the active substance is reduced. Alternatively, the air connection area is set up to apply a negative pressure to the clean room. This improves the safety of the clean room in such a way that, in particular, dangerous substances cannot escape from the clean room, particularly in the event of a leak.

The air connection region is also designed such that the interior of the clean room is also sealed in a sterile manner in the area of the closed or opened air connection region. The air connection region thus represents, in particular, a passage which can be sealed in a sterile manner for the supply and/or removal of air, in particular sterile air. "Sterile air" is not necessarily understood hereby, but at least also sterilized ambient air in a conventional composition. The term "sterile air" can also include other sterile gases suitable for use in the clean room, for example sterile inert gases, noble gases, carbon dioxide, nitrogen, or the like.

According to a development of the invention, it is provided that the shell is at least partially transparent. The shell preferably comprises a—preferably transparent—plastic or consists of such a plastic. This enables an optical control through the shell. In addition, such a clean room is particularly suitable as a disposable clean room, which can be disposed of after use, that is to say after the medicine container has been filled with the active substance and/or after the medicine container has been closed, without the costs being high. Preferably, therefore, the entire clean room or a part of the clean room—in particular the shell, and/or the manipulation device, and/or the active substance connection region, and/or the closing device, and/or the filling device, and/or the actuation connection region, and/or the air connection—are designed to be disposable and/or are intended for single use only.

According to a development of the invention, it is provided that the shell has at least one intervention device which can preferably be operated manually, in particular an intervention glove. Part of the shell is preferably designed as an intervention device. This part of the shell is thus designed for manual intervention, in particular, the intervention being able to be carried out in the interior of the clean room. Manual actions in the clean room are thus possible without opening the clean room.

According to a development of the invention, it is provided that a drive device can be assigned to the supply device, the drive device being operatively connected to the supply device, preferably via a conduit formed in the sleeve. The drive device is preferably set up to drive the preparation device for rotation and/or in a straight line, in particular linearly. In particular, the drive device can be operatively connected to the supply device such that the at least one medicine container and/or the at least one closure can be rotated, in particular pivoted, and/or in particular linearly displaced and/or displaced in height about an axis of rotation of the drive device and/or the supply device. The supply device can preferably be operatively connected, in particular is operatively connected, to a drive device such that the receiving device and/or the support elements of the provision device can preferably be rotated, raised and/or lowered independently of one another by means of the drive device. For this purpose, the drive device preferably has a shaft, in particular a multiple shaft, very particularly a hollow shaft, and a motor, in particular a servo motor. Using such a clean room, the filling of medicine containers is further automated and can therefore be carried out quickly and inexpensively.

The conduit is preferably designed to be airtight and sealed in a sterile manner, so that the drive device arranged outside the clean room can be connected to the supply device sealed in a sterile manner. It is in particular possible for the drive device to be able to be handled separately from the clean room, it being particularly preferred for it to be integrated in a laboratory table which is provided for use with the clean room. However, it is also possible for the drive device to be arranged in the clean room. The drive device can be designed to be energy self-sufficient and have an energy store, in particular an accumulator, also arranged in the clean room, so that no external active connection is required to actuate the drive device and thus also the supply device. However, it is also possible for the drive device arranged in the clean room to be supplied with energy via a sterile and airtightly sealed conduit. For example, the drive device can be designed as an electric motor, which can then be supplied with electrical power for driving the supply device in particular via a sterile and airtight electrical conduit.

According to a development of the invention, it is provided that the shell has at least one fastening element on its outside and/or at least one clamping element in its interior, in particular a hinged, inner support device for clamping the shell. By means of such a fastening element and/or such a clamping element, the clean room is in particular kept in its second functional state. This makes it particularly efficient to fill the medicine container. In addition, the displacement of the filling device and/or the displacement of the closing device are possible. In particular, the clean room can also be kept in its second, expanded functional state by means of such fastening elements and/or clamping elements when there is no excess pressure in the interior of the clean room. In particular, a negative pressure can even be formed in the interior of the clean room if the shell is held in its expanded form of the second functional state by external fastening elements and/or inner clamping elements. In this way, escape of hazardous substances, in particular infectious material, from the clean room into the external environment of the clean room can be prevented particularly effectively.

The object is also solved by providing a method for producing a transportable clean room especially according to one of the preceding embodiments. According to this method—preferably in an environment with a laminar air flow and/or with purity class A, B or C according to the EU GMP classification in the version applicable on the date determining the priority of the present application, at least one flexible shell element is provided, and an active substance connection region is arranged on the cover element. In addition, at least one actuation connection region, in particular a robot connection region, is arranged on the shell element. In addition, at least one medicine container, a manipulation device having a filling device and preferably at least one closure for the at least one medicine container are arranged on the flexible sleeve element and enclosed in an airtight manner with the at least one flexible shell element, so that an airtight, sterile shell is formed. The airtight enclosure forms an interior of the shell and separates it from an external environment in an airtight manner. The active substance connection region is preferably formed in the shell element or connected to the shell element. As an alternative or in addition, an air connection, in particular a sterile air connection, is arranged on the shell element, in particular is formed in the shell element or is connected to the shell element. In addition, a conduit is preferably formed in the shell element, through which a drive device which can be assigned to the clean room and can be operatively connected to a supply device arranged in the clean room can be conducted. The supply device is more preferably introduced into the clean room before the airtight enclosure with the shell. In addition, at least one fastening element is preferably provided in or on the casing. Such a method enables a transportable clean room to be produced particularly cost-effectively and efficiently. Due to the airtight enclosure, the risk of contamination of the clean room is also reduced, in particular if the clean room is transported, stored or used in a non-sterile environment. A non-sterile environment is understood here to mean in particular an area which has a lower purity, in particular therefore a higher particle density and/or a higher bacterial count than the interior of the clean room. A region with a purity class C or D—according to the EU GMP classification in the version valid on the day determining the priority of the present application—and/or an impure environment is particularly understood.

The at least one shell element is preferably cut in accordance with a cutting pattern such that the three-dimensional geometry provided for the clean room results when the at least one shell element is connected to seam regions provided for this purpose. It is possible for the shell of the clean room to be produced from a single shell element which is tightly connected at the seams provided for this purpose in order to enclose the components arranged in the clean room in an airtight manner. However, it is also possible for the shell to be formed from a plurality of shell elements, which are then tightly connected to one another in a corresponding manner. In particular, the at least one shell element is preferably first spread out flat so that the components to be arranged in the clean room can be arranged on the shell element. The at least one sleeve element is then deformed, in particular folded, in such a way that the seams to be connected to one another are brought into overlap or contact with one another, after which the at least one shell element is connected in an airtight and sterile manner at the provided seams. In this way, the closed shell for the clean room is produced.

According to one embodiment of the method, it is provided that the interior of the shell is subjected to a negative pressure, preferably a vacuum, in such a way that the shell collapses. Such a method has the advantage that a portable clean room with a particularly small volume is created. This clean room requires very little storage space and the cost of storage is reduced. In particular, it is possible and economical to produce and store a large number of such transportable clean rooms in stock, so that they can be removed from the storage room and the medicine containers filled at a later point in time when the demand for such transportable clean rooms is high.

According to a further alternative embodiment of the method, it is provided that the clean room is sterilized by means of superheated steam and/or protective gas and/or electromagnetic radiation, in particular gamma radiation, and/or particle radiation, in particular electron radiation. A particularly safe clean room is thus created and the risk of contamination of the clean room is reduced. In particular, it is provided to store the clean room in a non-sterile environment, the sterility or the purity of the clean room not being endangered.

The object is also achieved by creating a method for filling a medicine container in a transportable clean room according to one of the preceding exemplary embodiments. According to this method, the shell of the clean room is preferably brought into an expanded position by means of an internal support structure and/or an outer support structure and/or a pressurized, preferably gaseous medium introduced into the interior of the clean room. At least one active substance supply is also connected to the active substance connection region. Furthermore, an actuation device, in particular a robot, is connected to the actuation connection region, in particular the robot connection area. In addition, the filling device is preferably coupled to the active substance connection region—if it is not already coupled to it—and the active substance connection region is opened. The filling device and/or the medicine container are preferably arranged relative to one another in a position suitable for filling the medicine container, preferably by means of the manipulation device and/or the supply device. By actuating the filling device, an active ingredient is introduced into the medicine container. Furthermore, the method comprises opening the clean room by opening the shell, and removing the at least one at least partially filled medicine container. Such a method makes filling a medicine container particularly safe. In addition, the cost of filling using such a method is reduced.

The clean room is preferably arranged in a clean environment during filling, the clean environment preferably having a lower cleanliness class, very particularly cleanliness class B, C or D, than the interior of the clean room. The clean environment is preferably designed as a stationary clean room, which provides the actuating device, a drive device, an active ingredient supply and/or an air supply, in particular sterile air supply, for the clean room. This creates an additional safety mechanism which, in the event of a leak in the clean room, ensures that contamination of the clean room is at least reduced, in particular avoided. In addition, the costs are reduced compared to filling in the clean environment without the clean room.

Alternatively, the clean room is arranged in an impure environment during filling, the costs being particularly low and the method being flexible. Thanks to the clean room and the airtight enclosure with the cover, safety during filling is ensured even in an unclean environment.

The filling device is preferably coupled to the active substance connection region in such a way that the filling device is connected to the active substance supply in terms of flow, in particular for the automated filling of the medicine container. The shell is preferably separated by means of a destructive step; the shell is particularly preferably cut open. After the shell has been separated, the disposable parts of the clean room are preferably disposed of. Particularly preferably, the shell, hoses connected to the air connection region and/or the active substance connection, parts of the filling device intended for single use, in particular a filling needle, the air connection area and/or the active substance connection region are disposed of. After the at least one medicine container has been filled and before opening, the clean room is preferably brought into a sterile environment in order to be separated there, preferably after sterilization, and to manually close the medicine container. This further increases the safety of the method. In addition, the cost of the method is reduced, especially since parts of the method can be carried out in a non-sterile environment, and the risk of contamination is not increased.

According to one embodiment of the method, it is provided that the at least one medicine container is closed with a closure, in particular a stopper, before the shell of the clean room is opened. It is preferably provided that the closure is inserted into the medicine container or applied to the medicine container by means of the closing device of the manipulation device. This reduces the risk of contamination of the medicine container. In addition, the clean room can be arranged in the non-sterile environment during the entire process, in particular without an increased risk of contamination, so that the costs of the process are low.

According to a further alternative embodiment of the method, it is provided that an air supply, preferably a sterile air supply, is connected to an air connection area, preferably a sterile air connection area, of the clean room, the air connection region preferably being opened. It is further preferred that the air is filtered between the air supply and the air connection area by means of an air filter in the air supply and/or in the air connection region and/or in a connecting element, in particular an external and/or internal air hose. A slight positive pressure is particularly preferably generated by means of the air supply. This reduces the risk of contamination in the clean room. Alternatively, it is provided that a slight negative pressure is generated in the clean room by means of the air supply, so that the safety of the clean room is increased by preventing dangerous substances from escaping from the clean room.

According to a further embodiment, it is provided that an airtightness, a pressure and/or a purity, preferably a particle density and/or a bacterial count and/or a particle size distribution, of the clean room are monitored. The safety of the clean room is thus further increased in that a leak in the clean room, in particular in the shell of the clean room, which endangers the cleanliness of the clean room or the safety of the environment of the clean room, can be determined in a simple manner.

The descriptions of the clean room, the manufacturing process and the filling process are to be understood as complementary to each other. In particular, features of the clean room that have been described explicitly or implicitly in connection with the method for manufacturing and/or the method for filling are preferably individually or combined features of the clean room. The clean room is preferably designed to carry out at least one of the method steps described in connection with the method. Method steps that have been described explicitly or implicitly in connection with the clean room are preferably, individually or in combination with one another, steps of a preferred embodiment of the method for producing and/or the method for filling. In particular, at least one step, which results from at least one feature of the clean room, is preferably provided as part of the method for producing and/or the method for filling.

Overall, it can be seen that the transportable clean room shown here, the method for filling a medicine container in such a transportable clean room and the method for producing such a transportable clean room provide means for inexpensively supplying at least one medicine container, in particular filling a small number of medicine containers. In addition, the filling can be carried out particularly quickly by means of such a clean room and/or the method for filling, since the clean room—by means of the manufacturing process—can be produced in stock and can be stored compactly and inexpensively.

Such a transportable clean room can be used, for example, directly in a clinic, a hospital, a hospital ward or the like, in order to fill smaller amounts of medicinal active substances and/or auxiliary materials in a sterile manner, in particular for individual medical purposes, wherein such facilities as clinics, hospitals, hospital wards or the like often do not have their own clean rooms which meet a purity classification prescribed for the filling of medicine containers with the sterility required for this. The transportable clean room, on the other hand, can have this sterility on the inside, whereby it can be introduced into a less sterile environment and used there to fill medication containers in a sterile manner. Only when the medicine containers are closed in the clean room are they removed from it, so that there is no risk of contamination. The transportable clean room can also be used, for example, in crisis areas, for example in order to be able to provide antidotes to pathogens, chemical and/or biological warfare agents or the like quickly and in a sterile manner even in non-sterile environments. Vaccines can also be filled quickly and in a sterile manner in non-sterile environments. Overall, with the portable clean room proposed here, it is possible to fill and close in a sterile manner small quantities of medicine containers with the required sterility under environmental conditions that do not meet the sterility required for the filling of medicinal active substances and/or auxiliaries before they are then brought out of the clean room into the non-sterile or at least less sterile environment.

The invention will be explained in more detail below with reference to the drawing. The single FIGURE shows a schematic cross-sectional view of a transportable clean room according to an embodiment.

The single FIGURE shows a cross-sectional view of a transportable clean room 1, which is enclosed airtightly by a shell 3. The shell 3 is at least partially flexible. For the most part, the shell 3 is preferably flexible and preferably transparent.

In addition, the shell 3 has an openable active substance connection region 5 and an air connection region 7. A plurality of medicine containers 9 are arranged in the clean room 1, of which only one is provided with a reference symbol here for the sake of clarity. In addition, a manipulation device 11 is arranged in the clean room 1, which has a filling device 13 and a closing device 15. The filling device 13 is coupled to the active substance connection region 5, in particular connected to it in terms of flow technology by means of a hose 17. In the exemplary embodiment shown here, the filling device 13 also has a filling needle 19, by means of which the active substance can be introduced into the medicine container 9.

The closing device 15 is designed as a plug setting pin 21. The stopper pin 21 has a sleeve which can be inserted into the medicine container 9 and which is designed to receive an elastically compressible closure, in particular a stopper. The closing device 15 also has a retaining device for the stopper received in the sleeve. After insertion of the sleeve, which has received the stopper, into the medicine container 9, the stopper is held upward in the sleeve by the retaining device. By means of a relative displacement between the sleeve and the retaining device, the stopper can be removed from the sleeve and inserted into the medicine container 9, where it adheres due to its elasticity and closes the medicine container 9. During the relative displacement between the sleeve and the retaining device, the retaining device is preferably held stationary with respect to the medicine container 9 and the sleeve is led out of the medicament container 9, that is to say shifted upward in FIG. 1.

The shell 3 also has an actuation connection region 23, in particular a robot connection region, here in particular a robot flange. The filling device 13 and the closing device 15 can be actuated by means of an external actuating device 25, here in particular an external robot, which is connected, in particular flanged, to the actuating connection region 23 from the outside such that an active substance flow through the filling device 13 controls, in particular starts and stops, and the medicine container 9 can be closed by means of the closing device 15. In addition, the manipulation device 11 is set up to displace the filling device 13 and the closing device 15. In the exemplary embodiment shown here, the manipulation device 11 is displaced by means of the actuation device 25, the filling device 13 and the closing device 15 here being connected in a stationary manner to the manipulation device 11, and the manipulation device 11 being connected in a stationary manner to the actuation connection region 23. Thus, the filling device 13, the closing device 15, the manipulation device 11 and the actuation connection region 23 can be displaced together by means of the actuation device 25. The shell 3 is particularly flexible in the area around the actuation connection region 23. This ensures at least one displacement of the filling device 13 and the closing device 15 necessary for filling and closing the medicine container 9.

The clean room 1 also has a supply device 27 which provides the medication containers 9 and a plurality of closures 29 assigned to the medication containers 9, only one of which is provided with a reference number here. The closures 29, here in particular stoppers, are arranged in a closure matrix 31, here in a stopper matrix, preferably prepared. The medicine containers 9 are arranged in a tub 33, an opening 35 of the respective medicament container 9 facing the respectively associated closure 29 and/or the filling device 13 and/or being oriented upwards. The supply device 27 also has a plate system 37. The tub 33 with the medicine containers 9 is arranged on a lower plate 39, and the closure matrix 31 with the closures 29 arranged therein is arranged on an upper plate 41. The upper plate 41 and the lower plate 39 are rotatably mounted independently of one another about a preferably common axis A.

A drive device 43 is assigned to the supply device 27, the drive device 43 of the exemplary embodiment shown in FIG.

1 being designed as a servo drive. The drive device 43 is operatively connected to the supply device 27, in particular to the plate system 37 of the supply device 27, by means of a hollow shaft 45. Thus, the two plates 39, 41 of the supply device 27, that is to say the lower plate 39 and the upper plate 41, can be rotated about the axis A independently of one another by means of the hollow shaft 45 and a further shaft mounted therein. In addition, the drive device 43 is preferably set up to raise and lower the plates 39, 41 of the plate system 37 independently of one another.

The upper plate 41 preferably has for each closure matrix 31 one or a total of exactly one empty matrix, as seen in the circumferential direction, from the closure matrix 31, which, for example, can be spaced apart from the closure matrix 31 by 90° or 180° of the circumference of the upper plate 41. The empty matrix is preferably characterized by a number of openings in which no stoppers are arranged and through which the filling needle 19 can reach. The closures 29 and/or the openings of the empty matrix are preferably arranged exactly in a grid which corresponds to the grid in which the medicine containers 9 are arranged in the tub 33. Accordingly, if the closures 29 arranged in this grid are positioned above the medicine container 9, the closures 29 can be easily displaced through the closure device 15 into the medicine containers 9.

If, on the other hand, the empty matrix with the corresponding grid of openings is arranged above the medicine containers 9, the filling needle 19 can reach through the openings and fill the medicine containers 9 with the active substance.

Of course, it is also possible that instead of an empty matrix, a large opening, which in particular corresponds approximately to the areal extent of the tub 33, is arranged in the upper plate 41, or that the plate 41 is cut out in a suitable manner for filling the medicine containers 9.

The shell 3 of the clean room 1 also comprises a manually operable intervention device 47, here in particular an intervention glove. By means of this intervention device 47, it is possible to manually intervene in a filling process and/or to set up the manipulation device 11 and the supply device 27 in preparation for the filling process.

The shell 3 has on its outside a plurality of fastening elements 49, here in particular six fastening elements 49, for tensioning the shell 3. The fastening elements 49 in the exemplary embodiment shown here are designed as eyelets 51, which cooperate with hooks 55 fastened to a table 53 or to an external support structure (not shown here) in order to open the shell 3. For the sake of clarity, only one fastening element 49, one eyelet 51 and one hook 55 are provided with a reference symbol in FIG. 1.

Alternatively or additionally, the clean room 1 can also have an inner support structure arranged in the casing 3, by means of which it can be brought into the expanded functional state shown in the FIGURE and kept in this state, this expanded functional state also being referred to as the second functional state.

The clean room 1 can be evacuated via the air connection region 7, so that the shell 3 has a first, collapsed functional state. Accordingly, the shell 3 encloses a smaller volume than in the second functional state. A gas, in particular sterile air, can also be introduced into the shell 3 via the air connection region in order to bring it from the first functional state into the expanded second functional state. In the second functional state, the shell 3 can be kept under overpressure or under underpressure relative to an exterior.

The clean room 1 is preferably produced by providing at least one flexible shell element. The at least one active substance connection region 5 is then arranged on the shell element, and the at least one actuation connection region 23, in particular robot connection region, is arranged on the shell element. At least one medicine container, in particular a plurality of medicine containers 9, the manipulation device 11 with the filling device 13 and preferably at least one closure 29 for the at least one medicine container 9 are arranged on the at least one shell element. Then the at least one medicine container 9, the manipulation device 11, the filling device 13 and preferably the closure 29 are enclosed in an airtight manner with the at least one shell element, so that the shell 3 is formed which contains the medicine container 9, the manipulation device 11, the filling device 13, and preferably encloses at least one closure 29 airtightly.

The clean room 1 is preferably sterilized by means of superheated steam, a protective gas, electromagnetic radiation, and/or particle radiation, in particular electron radiation.

The medicine container 9 is filled in the clean room 1 by preferably first bringing the shell 3 into its expanded position, at least one active substance supply being connected to the active substance connection region 5, and the actuating device 25, in particular the robot, to the actuation connection region 23, in particular the robot connection region. If the filling device 13 is not already coupled to the active substance connection region 5, it is now coupled to the latter. The active substance connection region is then opened and at least one active substance is introduced into the medicine container 9 by actuating the filling device 13. The medicine container 9 is then preferably closed with a closure 29. If the medicine containers 9 are filled and closed, the clean room 1 is opened by opening the shell 3 and the at least one filled medicine container 9 is removed.

An air supply, in particular a sterile air supply, is preferably connected to the air connection region 7.

Overall, it can be seen that with the transportable clean room 1 shown here, at least one, in particular several, medicine containers 9 can be filled with an active ingredient in a particularly effective and cost-effective manner. The storage of such clean rooms 1 is also inexpensive and space-saving, especially if they are in their first functional state. In addition, the risk of contamination of the clean room 1 is reduced. With the clean room 1 proposed here, medicine containers 9 can also be filled in an environment which otherwise has insufficient sterility for filling medication containers 9. The clean room 1 can be used in particular for the production of small doses of active substances, for example for individual medicine, but can also be used for example in crisis regions for the rapid local provision of active substances, for example antidotes or vaccines.

The invention claimed is:

1. A clean room for filling at least one medicine container located in the clean room with at least one active substance, the clean room comprising:
  a shell for airtightly enclosing at least a portion of the clean room, the shell being at least partially flexible and having at least one active substance connection region which is openable and at least one actuation connection region;
  a manipulation device having at least one filling device coupleable to the at least one active substance connection region for introducing the at least one active substance into the at least one medicine container arranged in the clean room;
  an actuation device for actuating the manipulation device via the at least one actuation connection region of the shell, the actuation device operable to displace the at least one filling device relative to the at least one medicine container, actuate the at least one filling device, or both displace the at least one filling device and actuate the at least one filling device; and a drive device assigned to a provision device in the clean room, the drive device connectable with the provision device, wherein the clean room is a transportable clean room, wherein the at least one filling device comprises an actuatable filling device operable to control a flow of the at least one active substance; and wherein the shell has no openings for allowing the at least one medicine container to be introduced into the clean room.

2. The clean room according to claim 1, wherein the manipulation device has at least one closing device for closing the at least one medicine container with at least one closure arranged in the clean room and the manipulation device being configured for moving the at least one closing device relative to the at least one medicine container and/or for actuating the at least one closing device.

3. The clean room according to claim 2, further comprising a provision device arranged in the clean room, the provision device being configured to provide the at least one medicine container for filling via the at least one filling device and/or to provide the at least one medicine container for closing with the at least one closure, and/or the provision device being configured to provide the at least one closure for closing with the at least one closing device.

4. The clean room according to claim 2, wherein the at least one filling device, a closing device for closing the at least one medicine container with at least one closure, the manipulation device and the actuation connection region are displaceable together by the actuation device.

5. The clean room according claim 1, wherein the shell, in a first functional state of the clean room, encloses a first volume in an airtight manner, wherein, in a second functional state of the clean room, the shell encloses a second volume in an airtight manner, the second volume being larger than the first volume to accommodate filling of the at least one medicine container by the at least one filling device within the clean room.

6. The clean room according to claim 1, wherein the shell has at least one air connection region.

7. The clean room according to claim 6, wherein the at least one air connection region is selected from the group consisting of an openable region, a closable sterile air connection region and a combination thereof.

8. The clean room according to claim 1, wherein the drive device is connected to the provision device by a conduit formed on the shell.

9. The clean room according to claim 1, wherein the shell has at least one fastening element on an outside of the clean room and/or at least one clamping element in an interior of the clean room for clamping the shell.

10. The clean room according to claim 1, wherein the at least one filling device, a closing device for closing the at least one medicine container with at least one closure, the manipulation device and the actuation connection region are displaceable together by the actuation device.

11. The clean room according to claim 1, wherein the at least one medicine container is pre-arranged on at least one flexible shell element, and the shell of the clean room is formed by enclosing the at least one medicine container in an airtight manner with the at least one shell element, such that no openings are left for allowing any further medicine container to be introduced into the clean room.

12. The clean room according to claim 11, wherein the shell is formed by connecting the at least one shell element at predefined seams.

13. The clean room according to claim 1, wherein the shell is configured such that the at least one medicine container can be removed from the clean room after being filled only by destroying the shell.

14. A method for producing the transportable clean room of claim 1 comprising:

providing the shell to include at least one flexible shell element;

arranging the at least one active substance connection region on the at least one flexible shell element;

arranging at least one actuation connection region on the at least one flexible shell element;

arranging the least one medicine container, the manipulation device having the at least one filling device and at least one closure for the at least one medicine container on the at least one flexible shell element, and airtightly enclosing the at least one medicine container, the manipulation device, the filling device and the closure with the at least one flexible shell element, so that the shell is formed enclosing the at least one medicine container, the manipulation device, the filling device and the closure airtight.

15. A method for filling a medicine container in the clean room according to claim 1, the method comprising:

bringing the shell of the clean room into an expanded position with a gaseous medium introduced into an interior of the clean room;

connecting at least one active substance supply to the active substance connection region;

connecting an actuating device to the actuation connection region;

opening the active substance connection region;

introducing an active ingredient into the medicine container by actuating a filling device;

opening the clean room by opening the shell; and removing the medicine container.

16. A clean room for filling at least one medicine container located in the clean room with at least one active substance, the clean room comprising:

a shell for airtightly enclosing at least a portion of the clean room, the shell being at least partially flexible and having at least one active substance connection region which is openable and at least one actuation connection region;

a manipulation device having at least one filling device coupleable to the at least one active substance connection region for introducing the at least one active substance into the at least one medicine container arranged in the clean room; and an actuation device for actuating the manipulation device via the at least one actuation connection region of the shell, the actuation device operable to displace the at least one filling device relative to the at least one medicine container, actuate the at least one filling device, or both displace the at least one filling device and actuate the at least one filling device, wherein the clean room is a transportable clean room, wherein the at least one filling device comprises an actuatable filling device operable to control a flow of the at least one active substance, wherein the shell has no openings for allowing the at least one medicine container to be introduced into the clean room, and wherein the at least one active substance connection region of the shell is spaced from the at least one actuation connection region and the at least one filling device is connected to the at least one active substance connection region of the shell by a hose.

17. A clean room for filling at least one medicine container located in the clean room with at least one active substance, the clean room comprising:
   a shell for airtightly enclosing at least a portion of the clean room, the shell being at least partially flexible and having at least one active substance connection region which is openable and at least one actuation connection region;
   a manipulation device having at least one filling device coupleable to the at least one active substance connection region for introducing the at least one active substance into the at least one medicine container arranged in the clean room; and
   an actuation device for actuating the manipulation device via the at least one actuation connection region of the shell, the actuation device operable to displace at least one filling device relative to the at least one medicine container, actuate the at least one filling device, or both displace the at least one filling device and actuate the at least one filling device,
   wherein the clean room is a transportable clean room;
   wherein the manipulation device has at least one closing device for closing the at least one medicine container with at least one closure arranged in the clean room and the manipulation device being configured for moving the at least one closing device relative to the at least one medicine container and/or for actuating the at least one closing device;
   the clean room further comprising a provision device arranged in the clean room, the provision device being configured to provide the at least one medicine container for filling via the at least one filling device and/or to provide the at least one medicine container for closing with the at least one closure, and the provision device being configured to provide the at least one closure for closing with the at least one closing device;
   the clean room further comprising a drive device assigned to the provision device in the clean room, wherein the drive device is connectable with the provision device,
   wherein the shell has no openings for allowing the at least one medicine container to be introduced into the clean room.

18. The clean room according to claim 17, wherein the at least one active substance connection region of the shell is spaced from the at least one actuation connection region and the at least one filling device is connected to the at least one active substance connection region of the shell by a hose.

19. A clean room for filling at least one medicine container located in the clean room with at least one active substance, the clean room comprising:
   a shell for airtightly enclosing at least a portion of the clean room, the shell being at least partially flexible and having at least one active substance connection region which is openable and at least one actuation connection region;
   a manipulation device having at least one filling device coupleable to the at least one active substance connection region for introducing the at least one active substance into the at least one medicine container arranged in the clean room; and
   an actuation device for actuating the manipulation device via the at least one actuation connection region of the shell, the actuation device operable to displace the at least one filling device relative to the at least one medicine container, actuate the at least one filling device, or both displace the at least one filling device and actuate the at least one filling device,
   wherein the clean room is a transportable clean room,
   wherein the at least one filling device comprises an actuatable filling device operable to control a flow of the at least one active substance; and
   wherein the at least one active substance connection region of the shell is spaced from the at least one actuation connection region.

* * * * *